United States Patent [19]
Corbett

[11] Patent Number: 4,655,745
[45] Date of Patent: Apr. 7, 1987

[54] VENTRICULAR CATHETER

[76] Inventor: Joseph E. Corbett, 2134 Allen Blvd., Apt. 3, Middleton, Wis. 53562

[21] Appl. No.: 760,168

[22] Filed: Jul. 29, 1985

[51] Int. Cl.$^4$ ............................................. A61M 25/00
[52] U.S. Cl. ........................................ 604/49; 604/8; 604/96; 604/105
[58] Field of Search ................................ 604/49, 8–10, 604/96–106, 268; 128/344, 348.1

[56] References Cited

U.S. PATENT DOCUMENTS

| | | | |
|---|---|---|---|
| 2,470,665 | 5/1949 | Stiehl | 604/96 |
| 2,854,983 | 10/1958 | Baskin | 604/96 |
| 3,108,595 | 10/1963 | Overment | 604/105 |
| 3,241,554 | 3/1966 | Coanda | 604/105 |
| 3,435,827 | 4/1969 | Ericson | 604/268 |
| 3,626,950 | 12/1971 | Schulte | 604/268 |
| 3,669,116 | 6/1972 | Heyer | 604/268 |
| 3,690,323 | 9/1972 | Wortman et al. | 604/268 X |
| 4,141,364 | 2/1979 | Schultze | 128/344 X |
| 4,437,856 | 3/1984 | Valli | 604/96 X |

OTHER PUBLICATIONS

Garner Balloon Ventricular Catheter–Heyer, Schulte Corp. publication, 1971.

*Primary Examiner*—Dalton L. Truluck

[57] ABSTRACT

A catheter for controlling the drainage of fluid from a body cavity, particularly cerebrospinal fluid from the ventricle of human brain in the treatment of hydrocephalus. The catheter is in the form of an elongated, hollow conduit having a plurality of apertures formed at one end in communication with the hollow interior of the conduit. A barrier is mounted on the conduit adjacent the apertures and is located between the apertures and the outflow or opposite end of the conduit. Preferably, the barrier is in the form of a cuff which is inflatable after insertion into the ventricle of the brain to indicate to the surgeon that the inflow end of the catheter has been accurately positioned within the ventricle of the brain and to space the apertures in the inflow end of the catheter a sufficient distance from the surrounding brain tissue and choroid plexus to prevent the growth or adherence of surrounding tissue over the apertures in the conduit.

1 Claim, 7 Drawing Figures

1

VENTRICULAR CATHETER

BACKGROUND OF THE INVENTION

1. Field of the Invention

The present invention relates, in general, to surgical devices, specifically, to catheters or shunts for controlling the drainage of fluid between different areas of a human body and, more specifically, to catheters for draining cerebrospinal fluid from the cerebral ventricles to other areas of the body in the treatment of hydrocephalus.

2. Description of the Prior Art

Various types of shunts and catheters have been employed in surgical applications to control the flow of body fluids between various areas of a human body. Such shunts or catheters are extensively utilized in the treatment of hydrocephalus to overcome or control the lack of free circulation and/or absorption of cerebrospinal fluid within the brain.

In treating or controlling hydrocephalus, one end of a catheter is inserted through the skull into a cerebral ventricle of the brain, typically in a lateral ventricle of the brain. The opposite or outflow end of the catheter is attached to a valved shunt and directed either through the jugular vein toward the heart where the cerebrospinal fluid combines with blood or into the abdominoperetoneal cavity where the cerebrospinal fluid is absorbed by the peritoneal fluid into the bloodstream.

The catheter is typically in the form of a hollow tube which is provided with a plurality of apertures at the ventricular or inflow end to permit the passage of fluids from the brain into the catheter and thence to the bloodstream of the patient. However, malfunctions frequently occur with such a catheter due to the blockage of the apertures in the inflow end of the catheter. Such blockage is usually caused by the migration of choroid plexus tissue within the ventricle over the apertures in the inflow end of the catheter. This tissue may block the apertures in the inflow end of the catheter in a relatively short period of time after the catheter has been inserted into the ventricle thereby rendering the catheter inoperative in relieving excess pressure due to the build-up of cerebrospinal fluid within the ventricle.

The likelihood of this type of catheter malfunction can be lessened by properly placing the inflow end of the catheter carrying the apertures sufficiently far anteriorly in the lateral ventricle of the brain such that the apertures are beyond the anterior extent of the choroid plexus. This prevents the migration of the choroid plexus over the apertures in the catheter.

In addition, the inflow end of the catheter should be positioned anterior to the foramen of Munro. However, it is difficult for the surgeon to accurately locate the tip end of the catheter the proper distance away from the chorioid plexus to prevent the migration of the choroid plexus over the inflow end of the catheter and yet still remain in the ventricle.

Various attempts have been made to correct this problem. U.S. Pat. No. 3,690,323 discloses a catheter having an umbrella-shape cover over the apertured end which is inserted into the brain in a closed position and opened by extending the ribs of the cover outward into the ventricle. A gauze-like material is attached to the ribs and is porous to cerebrospinal fluid flow so as to enable flow into the apertures and, yet, prevent the growth of choroid plexus over the apertures. However, growth of choroid plexus or other brain tissue over the ribs and gauze material eventually results in total blockage of the apertured end of the catheter.

U.S. Pat. Nos. 3,886,948 and 3,894,541 show a catheter having a plurality of spaced, radially extending flanges which are mounted on the inflow end of the catheter. The flanges surround the apertures formed in the inflow end of the catheter to prevent the growth of the choroid plexus growth over the apertures. The ribs are formed of a flexible material which bends during insertion through the dura and substance of the brain. However, blockage of the apertures can still eventually occur and, further, the surgeon is not provided with an adequate indication of the position of the tip end of the catheter during insertion of the tip end into the ventricle of the brain.

Thus, the above-listed exemplary catheters which are utilized to treat hydrocephalus lack any means for indicating an accurate positioning of the tip end of the catheter within the ventricle at a position to space the tip end of the catheter carrying the apertures from the choroid plexus to prevent the growth of choroid plexus over the apertures in the catheter.

As such, it would be desirable to provide a catheter which overcomes the problems of previously devised ventricular catheters which are emplaceable within a ventricle of a human brain to control the flow of excess fluids from the brain in the treatment of hydrocephalus. It would also be desirable to provide a ventricular catheter which provides an indication to the surgeon that the tip end carrying the apertures on the ventricular catheter is accurately positioned a pre-determined distance away yet still is located within the ventricle to lessen the likelihood of growth of choroid plexus tissue over the apertures in the tip end of the catheter.

SUMMARY OF THE INVENTION

The present invention is a catheter which is suitable for insertion into the ventricle of the brain of a patient for controlling the drainage of excess fluid from the brain caused by hydrocephalus.

The catheter is formed in an elongated, hollow, flexible conduit having inflow and outflow ends. A plurality of apertures are formed in the inflow end of the catheter to enable fluid flow from the brain into the hollow interior of the conduit.

A barrier, preferably in the form of an expansible cuff, is mounted adjacent to the inflow end of the conduit between the apertures formed in the conduit and the outflow end of the conduit. The cuff may have a spherical form or may be provided with accordion-like folds to provide easy insertion into the ventricle when deflated and yet enable easy inflation to an expanded form after insertion into the ventricle.

In use, the catheter carrying the barrier cuff in its deflated form is inserted through a bore hole formed in the skull of the brain into the ventricle until cerebrospinal fluid issues from the outflow end of the catheter. A fluid, such as air, saline solution, water, etc., is injected through a tube attached to the exterior surface of the conduit in communication with the cuff to cause expansion of the cuff. The catheter is then urged or pulled outward by the surgeon until resistance is met indicating that the cuff has been brought into engagement with the interior surface of the solid brain tissue. This accurately positions the inflow end of the catheter carrying the apertures within the ventricle of the brain away from the anterior extent of the choroid plexus thereby lessening the likelihood of occlusion by choroid plexus material. Furthermore, the expansible cuff prevents occlusion of the apertures in the catheter by ventricular lining tissue when the ventricle become narrowed following drainage of cerebrospinal fluid from the brain.

BRIEF DESCRIPTION OF THE DRAWING

The various features, advantages and other features of the present invention will become more apparent by referring to the following detailed description and drawing in which.

DESCRIPTION OF THE PREFERRED EMBODIMENTS

Figure 1:
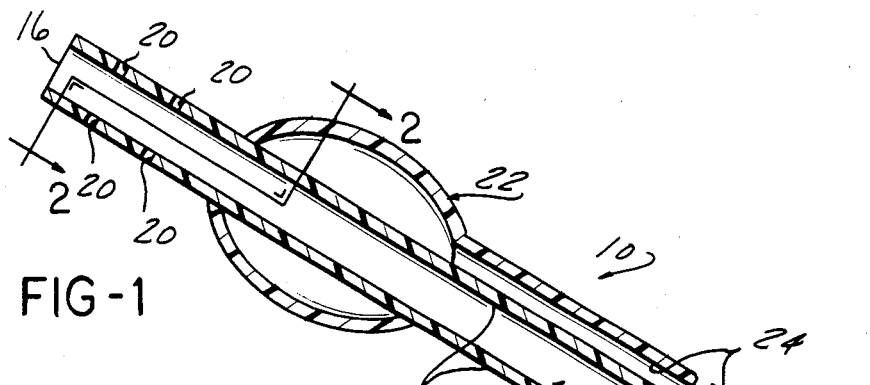
FIG. 1 is a cross-sectional view showing one embodiment of the ventricular catheter of the present invention.

Throughout the following description and drawing, an identical reference number is used to refer to the same component shown in multiple figures of the drawing.

Referring now to the drawing, there is illustrated a catheter 10 which is suitable for insertion into a lateral ventricle of a human brain to control the drainage of excess cerebrospinal fluid from the brain in a typical manner in the treatment of hydrocephalus. Since the present invention concerns only the construction of the catheter 10, a detailed description of the emplacement within the body of the patient of the outflow end of the catheter 10 in the jugular vein, peritoneal cavity or connection to exterior shunts or catheters will not be provided as such details are well known in the relevant surgical art.

The catheter 10 is formed of an elongated hollow conduit 12 having thin side walls 14, an inflow or first end 16 and an outflow or second, opposite end 18. The conduit 12 is formed of a thin, flexible material suitable for insertion into a human body.

A plurality of apertures 20 are formed adjacent the inflow or first end 16 of the conduit 12 and are disposed in communication with the hollow interior of the conduit 12. The apertures 20 provide access into the conduit 12 for excess fluid from the ventricle of the brain as will be described in greater detail hereafter.

Figure 2:
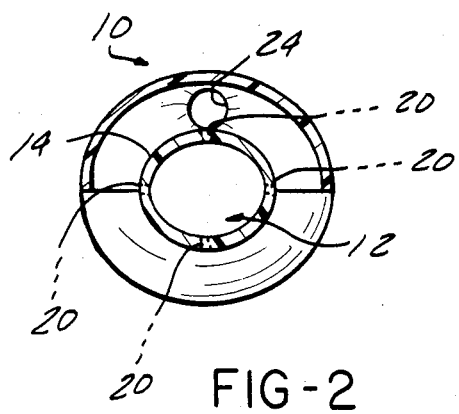
FIG. 2 is a cross-sectional view generally taken along 2—2 in FIG. 1.

The catheter 10 also includes a barrier means, such as an expansible means denoted in general by reference number 22, which is formed on the conduit 12 adjacent to the first or inflow end 16 and the apertures 20. The expansible means 22 is preferably in the form of a thin, expansible, hollow cuff or balloon which is integrally formed or joined to the side walls 14 of the conduit 16. An elongated tube 24 is attached to the exterior surface of the conduit 12 and is disposed in fluid communication with the interior of the hollow cuff 22. The cuff 22, when inflated will, as shown in FIGS. 1 and 2, assume a generally spherical configuration.

Figure 3:
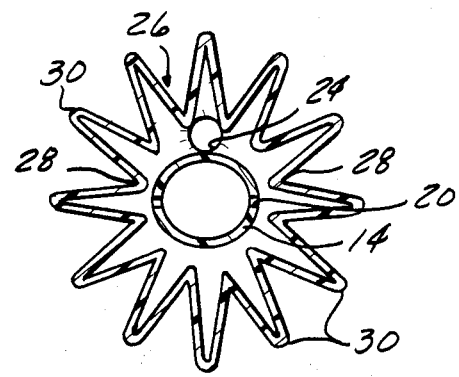
FIG. 3 is a cross-sectional view, similar to that shown in FIG. 2, but showing another embodiment of the cuff mounted on the ventricular catheter of the present invention.

Other configurations for the cuff 22 may also be provided as shown in FIG. 3. In this embodiment, the cuff 26 is provided with a plurality of crease lines 28 which form a plurality of outwardly extending, expansible and retractable zig-zag accordian-type folds 30 in the cuff 26. Upon inflation, the folds 30 can expand outward to form a general spherical cuff 26 around the inflow end of the conduit 12.

Figure 4:
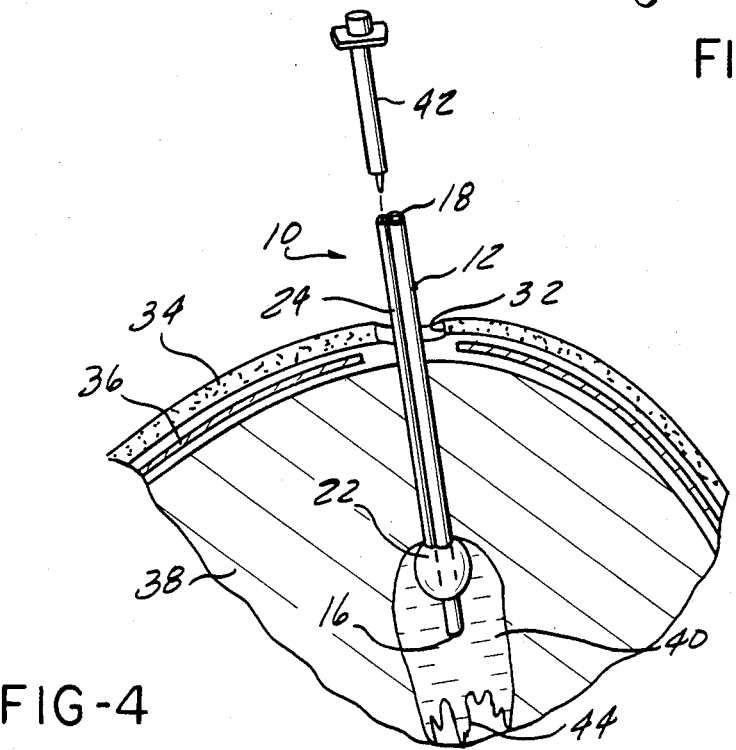
FIG. 4 is a pictorial representation of the use of the ventricular catheter of the present invention to control the drainage of excess fluid from the ventricle of a human brain.

Referring now to FIG. 4, the utilization of the catheter 10 of the present invention in controlling the drainage of fluid from various areas or cavities within a body, such as from a ventricle in the brain, will be described. As shown in FIG. 4, an opening or hole 32 is formed in the skull 34 of the brain through the dura 36 and the brain tissue 38 into the a lateral ventricle 40. The catheter 10 is inserted through the opening 32 in a deflated manner until the surgeon is certain that the inflow end 16 of the catheter 10 is positioned within the ventricle 40 of the brain. A syringe 42 containing a source of fluid, such as air, water, saline or other brain compatible fluid, is inserted into the tube 24 attached to the catheter 10 so as to cause inflation of the cuff 22 mounted on the catheter 10 adjacent the first or inflow end 16 of the catheter 10. Once inflated and the tube 24 clamped off, the surgeon can gently withdraw the catheter 10 from the ventricle 40 until the exterior surface of the inflated cuff 22 engages the walls of the ventricle 40. The resistance exerted by such engagement will indicate to the surgeon that the catheter 10 is properly positioned within the ventricle 40. A flow of cerebrospinal fluid through the conduit 12 will also indicate that the inflow end of the conduit 10 is accurately positioned within the ventricle 40 of the brain. This insures that the tip end 16 of the catheter 10 is spaced a sufficient distance from the choroid plexus 44 such that it could be unlikely that the choroid plexus 44 could occlude the inflow of cerebrospinal fluid through the apertures 20.

The inflated cuff 22 also forms a barrier which prevents choroid plexus 44 or the walls of the ventricle 40 from migrating or growing over the apertures 22 in the inflow end 16 of the catheter which had previously caused undesirable blockage of the apertures in the prior art catheters and have required the removal of the catheter 10 from the brain for replacement.

The outflow or second end 18 of the catheter 10 may be connected to a valved drainage shunt which would cause the fluid to eventually drain to the jugular vein or the peritoneal cavity in a conventional manner known in the art for treating hydrocephalus.

Figure 5:
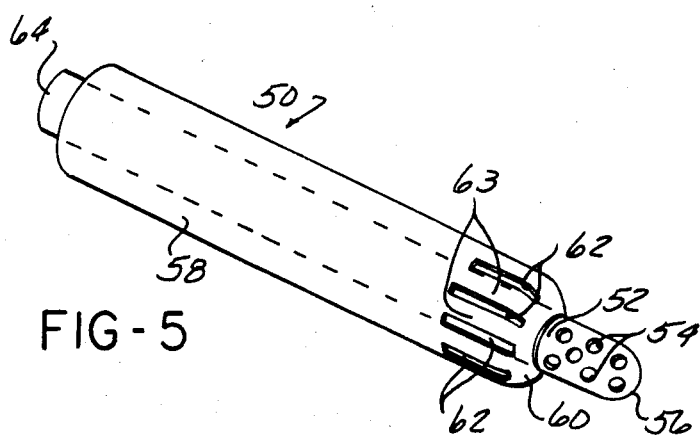
FIG. 5 is a perspective view of another embodiment of the ventricular catheter of the present invention.
Figure 6:
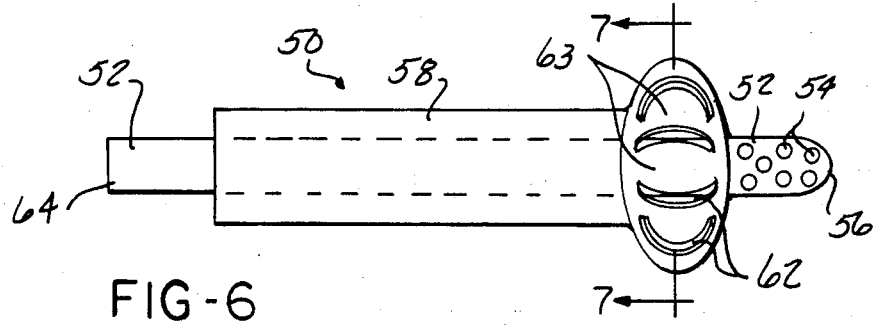
FIG. 6 is a side, elevational view of the embodiment shown in FIG. 5.

Another version of the catheter of the present invention is shown in FIGS. 5 and 6. In these figures a catheter 50 is provided with mechanical means for providing a barrier once the tip end of the catheter 50 is inserted into the ventricle of the brain.

The catheter 50 includes an inner conduit 52 having a plurality of apertures 54 formed at its tip or inflow end 56. The inner conduit 52 is surrounded by an outer conduit 58 of shorter length which is bonded at its frontmost end 60 to the exterior surface of the inner conduit 52 adjacent the apertures 54 in the tip end 56 of the conduit 52.

The outer conduit 58 is provided with a plurality of lengthwise extending slots 62 which create weakened strips 63 in the end of the outer conduit 58. The strips 63 are capable of bending when the inner conduit 52 is moved relative to the outer conduit 58 as shown in FIG. 6.

Upon use of the catheter 50 shown in FIGS. 5 and 6, the tip end 56 of the conduit 52 is inserted through a burr hole in the brain into the ventricle as described above. The surgeon then grasps the outflow end 64 of the conduit 52 and exerts an outward force on the conduit 52. Since the outer conduit 58 is formed of somewhat rigid material, the outward force and the connection between the frontmost end 60 of the outer conduit 58 and an intermediate portion of the conduit 52, will cause deformation of the strips 63 in the end of the conduit 58 between the slots 62. This will cause a radial expansion of the strips 63 surrounding the slots 62, as shown in FIG. 6, to form an expanded barrier or wall which can be brought into engagement by the surgeon with the brain tissue surrounding the ventricle. This enables accurate positioning of the tip end 56 of the catheter 50 within the ventricle of the brain and, at the same time, provides a barrier which minimizes or prevents the migration of the surrounding ventricle tissue or choroid plexus over the apertures 54 in the tip end 56 of the conduit 52.

Figure 7:
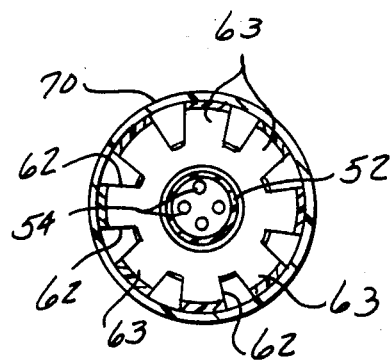
FIG. 7 is a cross sectional view generally taken along line 7—7 in FIG. 6, but showing the addition on an outer, porous membrane surrounding the expandable cuff.

As shown in FIG. 7, an alternate embodiment of the present invention may include an exterior, thin membrane 70 which may be porous or non-porous to fluid flow but which will prevent choroid plexis or ventricular lining tissue from becoming entrapped within the apertures 54 in the catheter 50 when it is necessary to remove the catheter 50 from the ventricle, during which the strips 63 will collapse into an aligned tubular form for easy removal. The membrane 70 may be attached by conventional means about the expansable end of the catheter 50.

In summary, there has been disclosed a unique catheter which provides a convenient and efficient means for controlling the drainage of fluid between various cavities within the body. The catheter of the present invention is uniquely suited for use in treating excess pressure build-up of cerebrospinal fluid within the ventricle of a human brain. A barrier in the form of an expansible cuff formed on the catheter enables the surgeon to accurately position the catheter within the ventricle and prevents the growth of choroid plexus tissue or ventricular lining tissue over the apertures formed in the end of the catheter thereby eliminating blockage of the catheter. This insures longer usefulness of the catheter once it has been emplaced within the brain.

What is claimed is:

1. A method for positioning a catheter in the ventricle of a brain comprising the steps of:

forming a burr hole through the skull of the brain into a ventricle of the brain;

inserting a flexible, hollow conduit having inflow and outflow ends with a plurality of apertures formed adjacent the inflow end disposed in fluid flow communication with the hollow interior of the conduit and having an inflatable cuff mounted on the conduit adjacent to the apertures and between the the apertures and the outflow end of the conduit into the ventricle of the brain;

injecting a fluid into the cuff to cause inflation of the cuff;

retracting the conduit after the cuff has been inflated through the bore hole in the brain until resistance is met to indicate that the cuff has engaged the walls of the ventricle of the brain and that the apertures in the conduit are spaced from the walls of the ventricle and the choroid plexus of the brain a sufficient distance to prevent the growth of choroid plexus over the apertures.

* * * * *